(12) United States Patent
Choi et al.

(10) Patent No.: US 9,095,643 B2
(45) Date of Patent: Aug. 4, 2015

(54) COMPOSITION PREVENTING TISSUE ADHESION AND PREPARATION METHOD THEREOF

(75) Inventors: Jin-suk Choi, Seoul (KR); Young-woo Lee, Gyeonggi-do (KR); Yun-gee Lee, Seoul (KR); Jun-ho Kim, Incheon (KR); Jin-ho Lee, Daejeon (KR)

(73) Assignees: Genewel Co., LTD (KR); Hannam University Institute Industry-Academia Cooperation (KR)

( * ) Notice: Subject to any disclaimer, the term of this patent is extended or adjusted under 35 U.S.C. 154(b) by 258 days.

(21) Appl. No.: 13/129,765

(22) PCT Filed: Sep. 17, 2009

(86) PCT No.: PCT/KR2009/005280
§ 371 (c)(1),
(2), (4) Date: May 17, 2011

(87) PCT Pub. No.: WO2010/058902
PCT Pub. Date: May 27, 2010

(65) Prior Publication Data
US 2011/0229432 A1    Sep. 22, 2011

(30) Foreign Application Priority Data
Nov. 19, 2008    (KR) .................... 10-2008-0114946

(51) Int. Cl.
*A61L 31/14*    (2006.01)
*A61L 31/04*    (2006.01)

(52) U.S. Cl.
CPC .............. *A61L 31/14* (2013.01); *A61L 31/041* (2013.01)

(58) Field of Classification Search
CPC ........ A61L 31/041; A61L 31/14; C08L 71/02
See application file for complete search history.

(56) References Cited

U.S. PATENT DOCUMENTS

| 4,188,373 A | 2/1980 | Krezanoski |
| 4,271,281 A * | 6/1981 | Kelley et al. ................... 526/80 |

(Continued)

FOREIGN PATENT DOCUMENTS

| JP | H08-231435 A | 9/1996 |
| JP | AH10-235230 | 9/1998 |

(Continued)

OTHER PUBLICATIONS

Ramadan H.H., "Surgical Causes of Failure in Endoscopic Sinus Surgery", Laryngoscope 109(1):27-29 (Jan. 1999).

(Continued)

*Primary Examiner* — Aradhana Sasan
(74) *Attorney, Agent, or Firm* — Swanson & Bratschun, L.L.C.

(57) ABSTRACT

Provided is a composition preventing tissue adhesion and a method for preparing the same, and, more particularly, a composition preventing tissue adhesion which further contains a drug selectively inhibiting inflammatory response and a method for preparing the composition, in which the composition is produced through a chemical reaction by adding a cross-linking agent to an aqueous solution which contains a block copolymer containing a polyethyleneoxide block having the ability to suppress tissue adhesion, and a polymer with 10,000 to 1,000,000 g/mol of molecular weight which can be mixed with the copolymer; the composition is characterized in that the difference of viscosity, absorbance of visible rays region, and stability between the upper and lower liquid layers are within 10% when centrifuging the composition; and also the method for preparing the composition enhances cross-linking homogenization and viscosity stability through simultaneous spraying and stirring methods without a reaction retardant.

15 Claims, 1 Drawing Sheet

(56) References Cited

U.S. PATENT DOCUMENTS

| | | | |
|---|---|---|---|
| 4,474,751 A | 10/1984 | Haslam et al. | |
| 4,478,822 A | 10/1984 | Haslam et al. | |
| 5,939,485 A | 8/1999 | Bromberg et al. | |
| 2005/0096445 A1* | 5/2005 | Fuchs et al. | 526/317.1 |
| 2007/0116666 A1 | 5/2007 | Cohn et al. | |

FOREIGN PATENT DOCUMENTS

| | | | | |
|---|---|---|---|---|
| JP | A2000-281794 | | 10/2000 | |
| JP | A2003-530136 | | 10/2003 | |
| JP | A2005-139293 | | 6/2005 | |
| KR | 10-0565881 | * | 1/2005 | A61K 31/765 |
| KR | 1020050011891 A | | 1/2005 | |
| KR | 10-0565881 | | 3/2006 | |
| KR | 10-2006-053279 | | 11/2006 | |
| WO | WO 90/04971 | | 5/1990 | |

OTHER PUBLICATIONS

International Search Report issued Apr. 28, 2010 in PCT/KR2009/005280.

Lee et al. (2005) "Tissue anti-adhesion potential of ibuprofen-loaded PLLA-PEG diblock copolymer films," Biomaterials, vol. 26, No. 6, pp. 671-678.

Kwon et al. (Oct. 2006) "Anti-adhesive Effect of Poloxamer/Alginate/$CaCl_2$ Mixture in the Rat Model," Journal of the Korean Surgical Society, vol. 71, No. 4, pp. 280-287.

Extended European Search Report issued Jul. 2, 2013 in EP Application No. 09827667.8.

Hercules (1999) "Aqualon Sodium Carboxymethylcellulose—Physical and Chemical Properties"

Molecular Probes (2008) Invitrogen MP 03000 "Pluronic® F-127"

* cited by examiner

COMPOSITION PREVENTING TISSUE ADHESION AND PREPARATION METHOD THEREOF

CROSS-REFERENCE(S) TO RELATED APPLICATIONS

The present invention is a national phase entry under 35 U.S.C. 371 of International Application No. PCT/KR2009/005280, filed on Sep. 17, 2009, which claims the benefit of Korean Patent Application No. 10-2008-0114946, filed on Nov. 19, 2008. The disclosures of said applications are incorporated by reference herein.

BACKGROUND OF THE INVENTION

1. Field of the Invention

The present invention relates to a composition preventing tissue adhesion and a method for preparing the same, and, more particularly, a composition preventing tissue adhesion which further contains a drug selectively inhibiting inflammatory response and a method for preparing the composition, in which the composition is produced through a chemical reaction by adding a cross-linking agent to an aqueous solution which contains a block copolymer containing a polyethyleneoxide block having the ability to suppress tissue adhesion, and a polymer with 10,000 to 1,000,000 g/mol of molecular weight which can be mixed with the copolymer; the composition is characterized in that the difference of viscosity, absorbance of visible rays region, and stability between the upper and lower liquid layers are within 10% when centrifuging the composition; and also the method for preparing the composition enhances cross-linking homogenization and viscosity stability through simultaneous spraying and stirring methods without a reaction retardant.

2. Description of Related Art

An adhesion is causing after various surgeries and is more strongly created by making tissue through a penetration of cell after making a first adhesion with surroundings organs or tissues from the effusion and coagulation of blood during the cure period of wound, such as an inflammation, a cut, a friction, a cut by a surgery, and the like. When generating an adhesion on a pelvis, a chronic pain, a sexual dysfunction, a sterility, and the like may be caused; the adhesion caused by a cicatrization after removing a thyroid causes a side effect, such as a chest pain, a decline of swallow ability, and the like; and the adhesion caused by spine surgery causes a sharp pain due to a neurothlipsis. Therefore, a second surgery may be required for removing the adhesions as mentioned above so that the financial burden has been increased and it is reported that the cost used for treating complications due to the adhesion after an adnominal operation is about 12 hundred million according to USA statistical data in 1988. It is known that a closure of small intestine is about 49 to 74%, sterility is about 15 to 20%, a chronic pelvis pain is about 20 to 50%, and an enterobrosis on a following surgery is about 19% as the complications caused by the adhesion after an abdominal operation. In addition, a recurrence rate is about 7.6 to 38% of patients after an endoscopy of the nasal cavity for treating a chronic sinusitis of an ear-nose-throat department. Also, it is reported that according to 'Ramadan' Thesis disclosed on Laryngoscope Journal (Laryngoscope, Jan.; 109(1): p. 27~29 (1999), Ramadan H. H., "Surgical causes of failure in endoscopic sinus surgery."), the adhesion is generated in 56% of the patients that have a re-operation due to the above reason. In the case of gynecology, the adhesion in the endometrium is generated at 20 to 50% after a suction evacuation or an exochleation due to a defective miscarry, a stillbirth, a recurrent miscarry, and the like, and it is known that a sterility, an amenorrhea, a habitual abortion, and the like are caused by the above adhesion so that many researches are being carried out to prevent the adhesion. Currently, a method using a physical barrier is developed and then in use.

It is well known that for a polyethylene glycol-polypropylene glycol-polyethylene glycol (PEC-PPG-PEG) block copolymer, its state is changed due to heat, such that its viscosity is changed according to the response to the environment stimulation, such as acidity, a temperature, an ion capacity, and the like, and is increased from a solution state to a gel state. Therefore, the techniques for using as a material for medical using the above features are disclosed in U.S. Pat. No. 5,939,485, No. 4,188,373, No. 4,478,822, No. 4,474,751, and the like.

Korean Patent No. 10-2003-0050953 among the conventional techniques related to a preventing agent of tissue adhesion discloses using a high-speed stirrer to cross-link the copolymer giving a proper viscosity and stability in a liquid solution by using one or more cation selected from the group consisting of $Mg^{2+}$, $Ca^{2+}$, $Sr^{2+}$ and $Ba^{2+}$ and one or more selected from the group consisting of chitosan, glutaraldehyde, formalin, and poly-L-lysine, but floating debris on a fiber are generated when preparing in a mass production and it is hard to remove the floating debris and also to make even cross-linking.

Korean Patent No. 10-2006-0053279 discloses a method for making even cross-linking by adding one reaction retardant selected from the group consisting of sodium carbonate ($Na_2CO_3$), trisodium phosphate ($Na_3PO_4$), hydrated trisodium phosphate ($Na_3PO_4 12H_2O$), sodium polyphosphate ($Na_5P_3O_{10}$), tetrasodium pyrophosphate ($Na_4P_2O_7$), hydrated tetrasodium pyrophosphate ($Na_4P_2O_7 10H_2O$), and hydrated ethylene diamine tetra acetic acid tetrasodium ($Na_4EDTA2H_2O$) as a reaction retardant for an ion-exchange polymerization, but the method is not suitable for a human body.

As mentioned above, it could not be prevented that the floating debris on a fiber generated due to uneven cross-linking up to now, and it could not be prepared that a composition preventing tissue adhesion can increase even cross-linking and stability of the viscosity.

SUMMARY OF THE INVENTION

In order to solve the above problems as mentioned above, an object of the present invention is to provide a composition preventing tissue adhesion which has an excellent ability for preventing tissue adhesion and can easily be applied to a wound on a human body, in which the composition is produced through a chemical reaction by adding a cross-linking agent to an aqueous solution containing a block copolymer having a polyethyleneoxide block with an excellent ability to suppress tissue adhesion and a biocompatibility and a polymer giving a proper viscosity and stability on the aqueous solution, and the composition further includes a drug selectively inhibiting inflammatory response.

In addition, the present invention provides a method for preparing the composition preventing tissue adhesion that can increase an even of cross-linking and stability of viscosity by using simultaneously spraying and stiffing methods without a reaction retardant when preparing the composition preventing tissue adhesion.

The above objects according to the present invention and other objects can be achieved by the present invention as disclosed in the following sentences.

DESCRIPTION OF SPECIFIC EMBODIMENTS

Figure 1:
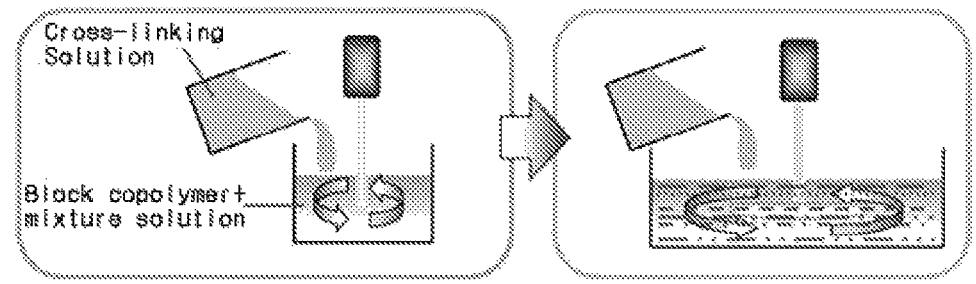
FIG. 1 shows a preparing method of Comparative Example 1 in accordance with an embodiment of the present invention.
Figure 2:
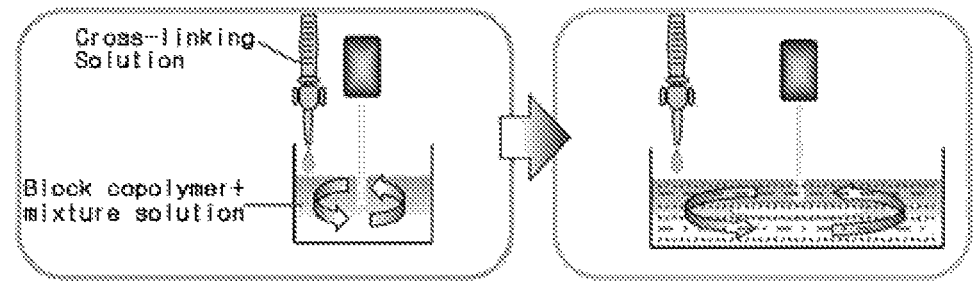
FIG. 2 shows a preparing method of Comparative Example 2 in accordance with an embodiment of the present invention.
Figure 3:
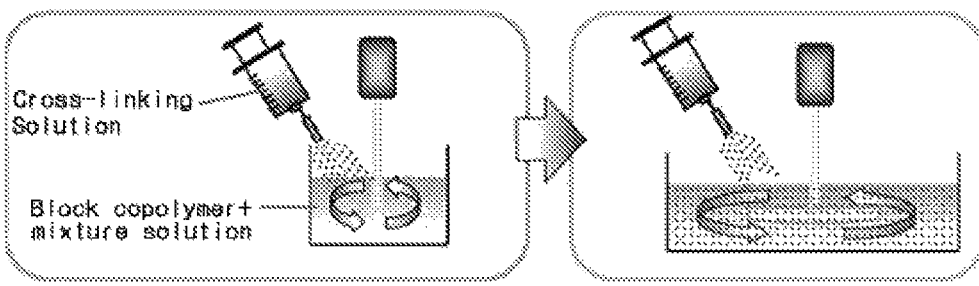
FIG. 3 shows a preparing method of Example 1 to Example 4 in accordance with an embodiment of the present invention.

In order to achieve the above objects, the present invention provides a composition preventing tissue adhesion that is characterized in that the differences of absorbance of visible rays region and stability between the upper and lower liquid layers are within 10% when centrifuging the composition for 3 minutes at 3,000 rpm and 25° C., in which the composition is produced through a chemical reaction by adding c) a cross-linking agent to an aqueous solution containing:

a) a block copolymer with 1,000 to 500,000 g/mol of molecular weight having a polyethyleneoxide block; and b) a polymer with 10,000 to 1,000,000 g/mol of molecular weight which can be mixed with the a) copolymer.

In addition, the present invention provides a method for preparing the composition preventing tissue adhesion, in which the method includes:

preparing the aqueous solution containing:
a) a block copolymer with 1,000 to 500,000 g/mol of molecular weight having a polyethyleneoxide block; and
b) a polymer with 10,000 to 1,000,000 g/mol of molecular weight which can be mixed with the a) copolymer; and then
simultaneously spraying and stirring c) the cross-linking agent in the range of 5 to 500 µm of spraying particle diameter to the aqueous solution.

As mentioned above, the composition preventing tissue adhesion according to the present invention can prevent the floating debris on a fiber caused by uneven cross-linking without adding a reaction retardant because total area of a surface of cross-linking agent can be maximized by using a method of spraying when preparing the composition, and also can increase the viscosity stability and cross-linking homogenization so that the composition preventing tissue adhesion can be very evenly applied to a wound on a human body, and has an excellent stability.

Hereinafter, the present invention will be described in detail.

The present invention provides a composition preventing tissue adhesion in order to achieve the above objects, in which the composition is prepared through a chemical reaction by adding a cross-linking agent to an aqueous solution containing a block copolymer having a polyethyleneoxide block that has an ability to suppress tissue adhesion, shows sol-gel transition according to the temperature after dissolving in the aqueous solution, and has 1,000 to 500,000 g/mol of molecular weight; and a polymer with 10,000 to 1,000,000 g/mol of molecular weight that can give proper viscosity (3,000 to 9,000 cP) and stability in the aqueous solution by mixing with the copolymer; the differences of viscosity, absorbance of visible rays region, and stability between the upper and lower liquid layers are within 10% when centrifuging the composition for 3 minutes at 3,000 rpm and 25° C.; and also the composition may selectively include a drug, especially, an anti-inflammatory.

In addition, the present invention provides a method for preparing the composition preventing tissue adhesion, in which the method includes:

preparing the aqueous solution containing:
a) a block copolymer with 1,000 to 500,000 g/mol of molecular weight having a polyethyleneoxide block; and
b) a polymer with 10,000 to 1,000,000 g/mol of molecular weight which can be mixed with the a) copolymer; and then
simultaneously spraying and stiffing c) the cross-linking agent in the range of 5 to 500 µm of spraying particle diameter to the aqueous solution.

The block copolymer containing the polyethyleneoxide block has 1,000 to 500,000 g/mol of molecular weight, and may include polyethylene-polypropylene oxide copolymer (Pluronic series), polyethyleneoxide-polylactic acid copolymer, polyethyleneoxide-polylacticglycolic acid copolymer, polyethyleneoxide-polycaprolactone copolymer, and the like.

The polymer with 10,000 to 1,000,000 g/mol of molecular weight may include one or more mixture selected from the group consisting of a type of glycosaminoglycan, such as chondroitin sulfate, dermatan sulfate, keratan sulfate, heparan sulfate, alginic acid, hyaluronic acid, carboxymethyl cellulose, dextran, collagen, and a resolvent of collagen such as gelatin, elastin, and fibrin.

At this time, the cross-linking agent may include a compound containing one or more cations selected from $Mg^{2+}$, $Mn^{2+}$, $Ca^{2+}$, $Cu^{2+}$, $Sr^{2+}$, $Ba^{2+}$, $Fe^{2+}$, and $Co^{2+}$; chitosan, glutaraldehyde, formalin, poly-L-lysine, acrylic acid polymers such as polyacrylic acid or polymethacrylic acid; a hydroxylamine compound such as dopamine; isoleucine, phenylalanine, leucine, threonine, lysine, tryptophan, methionine, valine, histidine, alanine, arginine, asparagine, aspartate, cysteine, glutamine, glutamate, glycine, proline, serine, tyrosine, and the like.

The composition preventing tissue adhesion according to the present invention is prepared by a chemical bond between the polymer and the block copolymer containing the polyethyleneoxide block, and the chemical bond may be formed by bonding through a graft co-polymerization, a random co-polymerization, a crosslink co-polymerization, a cross-linking, and the like.

In addition, the drug may include thrombin, aprotinin, steroidal anti-inflammatory drugs and nonsteroidal anti-inflammatory drugs (NSAIDs), heparin, tissue plasminogen activator, and the like.

The drugs may be included to the composition before applying on the wound or during preparing the composition preventing tissue adhesion according to the present invention, and the release of drug may be performed by a gelation the composition preventing tissue adhesion due to the body temperature.

When producing the composition preventing tissue adhesion by further adding the drugs, especially the anti-inflammatory, the drugs are released or the inflammatory response is suppressed so that the ability to suppress tissue adhesion can be more improved.

For producing the composition preventing tissue adhesion according to the present invention, any one selected from the group consisting of a saline solution, and a salt solution, such as phosphate buffer solution, organic salts buffer solution, bicarbonate buffer solution, and the like may be used because those solutions have an excellent biocompatibility as compared with the composition by using pure water since a body fluid is a solution containing a fixed quantity of salt. Especially, when using a salt solution, the temperature for the gelation can be decreased and the velocity can be reduced as compared with the composition produced by using pure water.

The content of the block copolymer containing the polyethyleneoxide block may be preferably 1 to 50 wt %, and more preferably 10 to 30 wt % based on the composition according to the present invention (hereinafter, called as 'the composition according to the present invention') produced from the aqueous solution containing the block copolymer having the polyethyleneoxide block, the polymer and the cross-linking agent. When the content thereof is less than 1 wt %, there is a problem such that the sol-gel transition is not occurred; and when the content thereof exceeds 50 wt %, there is a problem such that it is difficult to evenly apply on a body due to high viscosity of sample.

The content of the polymer in the composition according to the present invention may be preferably 0.1 to 4 wt %, and more preferably 0.5 to 1 wt %. When the content is less than 0.1 wt %, there are problems that it cannot give the viscosity and stability, or cannot form the cross-linking; and when the content exceeds 4 wt %, there is a problem that it is difficult to evenly apply on a body due to high viscosity of sample.

In addition, when cross-linking the polymer, the content of the cross-linking agent may be preferably 0.01 to 2 wt %, and more preferably 0.05 to 0.2 wt % based on the composition according to the present invention. When the content is less than 0.01 wt %, there is a problem such that it cannot form the cross-linking; and when the content exceeds 2 wt %, there is a strong cross-linking thereby not having a fluidity so that it is hard to inject into a body and apply on a body.

When the drug is added to the composition preventing tissue adhesion, the content of the drug may be preferably 0.01 to 50 wt %; and when using especially the anti-inflammatory as the drug, it may be more preferably 1 to 10 wt % based on the composition according to the present invention. When the content is less than 0.01 wt %, there is a problem such that the effects to suppress inflammatory response and prevent the adhesion, are not occurred; and when the content exceeds 50 wt %, there is a problem such that it is to be toxic on a human body.

When centrifuging the composition preventing tissue adhesion according to the present invention for 3 minutes at 3,000 rpm and 25° C. by using a centrifugal separator, the differences of viscosity, absorbance of visible rays region, and stability between the upper and lower liquid layers may be within 10%, preferably within 7%, and more preferably within 5%. The viscosity is measured at 20° C. that is in a sol state, the absorbance is measured at 400 to 750 wavelength region among the visible rays region, and the stability is measured by confirming the maintenance of gel state for 1 week after shaking at 60 rpm velocity after filling a saline solution having 37° C. at 37° C. that is a condition of human body.

The block copolymer containing the polyethyleneoxide block with the ability to suppress tissue adhesion and the polymer giving the viscosity and stability in the aqueous solution along with the copolymer according to the present invention are uniformly mixed, and also the composition preventing tissue adhesion produced by adding selectively the drug can be easily and evenly injected and applied to any complex wound, and has the stability so that it can be more effectively applied as an agent preventing tissue adhesion by having the excellent ability preventing tissue adhesion.

For producing the composition preventing tissue adhesion according to the present invention, the spraying velocity may be preferably 10 to 100 ml/min, and more preferably 50 to 100 ml/min when using the spraying method for applying the cross-linking agent.

When using the spraying method in the present invention, the cross-linking agent may be used by spraying in the range of 5 to 500 μm spraying particle diameter, and preferably in the range of 50 to 100 μm.

For producing the composition preventing tissue adhesion according to the present invention, the stiffing velocity may be preferably 300 rpm to 1500 rpm, and more preferably 500 to 1,000 rpm in the aqueous solution. When the stirring velocity is less than 300 rpm, a partial stirring can be occurred rather than an overall stirring.

Hereinafter, the present invention will be described in more detail in response to Examples, but it is only for understanding a detailed invention and is not limited to the following Examples.

EXAMPLE

Hereinafter, the present invention will be described in more detail in response to Examples, but it is only for understanding a detailed invention and is not limited to the following Examples.

Comparative Example 1

A polyethyleneoxide-polypropylene oxide copolymer that can suppress tissue adhesion, and has a biocompatibility and a sol-gel phase transition phenomenon was added in 25 wt % based on a composition according to the present invention to an aqueous solution that was dissolved with hyaluronic acid that is a natural polymer and has an excellent biocompatibility in 0.8 wt % based on a ultra-pure water; and then $Ca(CH_3COO)_2$ aqueous solution was added without any devices while stiffing at 500 rpm velocity by using a stirrer to produce a composition preventing tissue adhesion.

Comparative Example 2

A polyethyleneoxide-polypropylene oxide copolymer that can suppress tissue adhesion, and has a biocompatibility and a sol-gel phase transition phenomenon was added in 25 wt % based on a composition according to the present invention to an aqueous solution that was dissolved with hyaluronic acid that is a natural polymer and has an excellent biocompatibility in 0.8 wt % based on a ultra-pure water; and then $Ca(CH_3COO)_2$ aqueous solution was added in an amount of 20 ml/min by using a burette while stiffing at 500 rpm velocity by using a stirrer to produce a composition preventing tissue adhesion.

Example 1

A polyethyleneoxide-polypropylene oxide copolymer that can suppress tissue adhesion, and has a biocompatibility and a sol-gel phase transition phenomenon was added in 25 wt % based on a composition according to the present invention to an aqueous solution that was dissolved with hyaluronic acid that is a natural polymer and has an excellent biocompatibility in 0.8 wt % based on a ultra-pure water; and then $Ca(CH_3COO)_2$ aqueous solution was sprayed in an amount of 20 ml/min by using a spray while stirring at 500 rpm velocity by using a stirrer to produce a composition preventing tissue adhesion.

Example 2

A polyethylene oxide-polypropylene oxide copolymer that can suppress tissue adhesion, and has a biocompatibility and a sol-gel phase transition phenomenon was added in 25 wt % based on a composition according to the present invention to an aqueous solution that was dissolved with hyaluronic acid that is a natural polymer and has an excellent biocompatibility in 0.8 wt % based on a ultra-pure water; and then $CaCl_2$ aqueous solution was sprayed in an amount of 20 ml/min by using a spray while stirring at 500 rpm velocity by using a stirrer to produce a composition preventing tissue adhesion.

Example 3

A polyethyleneoxide-polypropylene oxide copolymer that can suppress tissue adhesion, and has a biocompatibility and a sol-gel phase transition phenomenon was added in 25 wt % based on a composition according to the present invention to an aqueous solution that was dissolved with alginic acid that is a natural polymer and has an excellent biocompatibility in 0.8 wt % based on a ultra-pure water; and then $Ca(CH_3COO)_2$ aqueous solution was sprayed in an amount of 20 ml/min by using a spray while stirring at 500 rpm velocity by using a stirrer to produce a composition preventing tissue adhesion.

Example 4

A polyethyleneoxide-polypropylene oxide copolymer that can suppress tissue adhesion, and has a biocompatibility and a sol-gel phase transition phenomenon was added in 25 wt % based on a composition according to the present invention to an aqueous solution that was dissolved with alginic acid that is a natural polymer and has an excellent biocompatibility in 0.8 wt % based on a ultra-pure water; and then $CaCl_2$ aqueous solution was sprayed in an amount of 20 ml/min by using a spray while stirring at 500 rpm velocity by using a stirrer to produce a composition preventing tissue adhesion.

After centrifuging the compositions preventing tissue adhesion of Comparative Example 1, Comparative Example 2, Example 1 to Example 4 produced by using the methods as mentioned above by using a centrifugal separator for 3 minutes at 3,000 rpm and 25° C., the upper and lower liquid solutions were separated and then the viscosity, absorbance of visible rays region and stability were measured. The results measured were shown in the following Tables 1, 2 and 3, respectively.

Table 1 shows the differences of viscosity after separating the samples produced in Comparative Examples 1, 2, and Examples 1 to 4 of the present invention into the upper and lower liquid layers by using the centrifugal separator.

Table 2 shows the absorbance of visible rays region after separating the samples produced in Comparative Examples 1, 2, and Examples 1 to 4 of the present invention into the upper and lower liquid layers by using the centrifugal separator.

Table 3 shows the stabilities after separating the samples produced in Comparative Examples 1, 2, and Examples 1 to 4 of the present invention into the upper and lower liquid layers by using the centrifugal separator.

TABLE 1

|  | Com. Ex. 1 | Com. Ex. 2 | Ex. 1 | Ex. 2 | Ex. 3 | Ex. 4 |
| --- | --- | --- | --- | --- | --- | --- |
| Upper(cP) | 1264 | 1320 | 1533 | 1492 | 1516 | 1460 |
| Lower(cP) | 1976 | 1620 | 1600 | 1544 | 1582 | 1532 |

As shown in the above Table 1, it could be known that the compositions preventing tissue adhesion of Example 1 to Example 4 produced by spraying a cross-linking agent by using a spray method had an excellent stability and the viscosity of the upper and lower liquid layers were similar each other so that the difference was within 10% as compared with Comparative Example 1 and Comparative Example 2 by not using the spray method.

TABLE 2

|  |  | 400 wavelength | 450 wavelength | 500 wavelength | 550 wavelength | 600 wavelength | 650 wavelength | 700 wavelength | 750 wavelength |
| --- | --- | --- | --- | --- | --- | --- | --- | --- | --- |
| Com. Ex. 1 | Upper(Abs) | 0.0492 | 0.0302 | 0.2286 | 0.0194 | 0.0150 | 0.0130 | 0.0110 | 0.0081 |
|  | Lower(Abs) | 2.0912 | 1.9172 | 1.7824 | 1.6495 | 1.5327 | 1.4233 | 1.3222 | 1.2293 |
| Com. Ex. 2 | Upper(Abs) | 0.8402 | 0.6877 | 0.5824 | 0.5060 | 0.4431 | 0.3940 | 0.3631 | 0.3177 |
|  | Lower(Abs) | 1.4994 | 1.2952 | 1.1437 | 1.0235 | 0.9309 | 0.8499 | 0.7808 | 0.7212 |
| Ex. 1 | Upper(Abs) | 0.9226 | 0.7762 | 0.6675 | 0.5837 | 0.5177 | 0.4596 | 0.4140 | 0.3777 |
|  | Lower(Abs) | 0.9750 | 0.8087 | 0.6902 | 0.5998 | 0.5271 | 0.4694 | 0.4205 | 0.3814 |
| Ex. 2 | Upper(Abs) | 0.9440 | 0.7878 | 0.6769 | 0.5912 | 0.5209 | 0.4643 | 0.4160 | 0.3765 |
|  | Lower(Abs) | 0.9558 | 0.7954 | 0.6796 | 0.5917 | 0.5236 | 0.4647 | 0.4187 | 0.3799 |
| Ex. 3 | Upper(Abs) | 1.0590 | 0.8680 | 0.7336 | 0.6331 | 0.5542 | 0.4911 | 0.4394 | 0.3941 |
|  | Lower(Abs) | 1.0683 | 0.8733 | 0.7403 | 0.6408 | 0.5621 | 0.5008 | 0.4506 | 0.4052 |
| Ex. 4 | Upper(Abs) | 1.0346 | 0.8521 | 0.7222 | 0.6251 | 0.5471 | 0.4855 | 0.4347 | 0.3905 |
|  | Lower(Abs) | 1.0210 | 0.8433 | 0.7181 | 0.6248 | 0.5486 | 0.4901 | 0.4413 | 0.3983 |

As shown in the above Table 2, it could be known that after centrifuging the compositions of Comparative Example 1 and Comparative Example 2 by not using the spray method, the difference of absorbance of visible rays region between the upper and lower liquid layers was large, but after the compositions preventing tissue adhesion of Example 1 to Example 4 produced by spraying a cross-linking agent by using a spray method, absorbance of visible rays region between the upper and lower liquid layers was similar so that the difference was within 10% and its cross-linkage degree was uniformed.

TABLE 3

|  |  | 0 Day | 1 Day | 2 Day | 3 Day | 5 Day | 7 Day |
| --- | --- | --- | --- | --- | --- | --- | --- |
| Com. Ex. 1 | Upper (%) | 100.0 | 89.7 | 79.5 | 69.2 | 59.0 | 38.5 |
|  | Lower (%) | 100.0 | 97.3 | 93.3 | 88.0 | 84.0 | 66.7 |
| Com. Ex. 2 | Upper (%) | 100.0 | 91.0 | 82.1 | 73.1 | 64.1 | 44.9 |
|  | Lower (%) | 100.0 | 94.7 | 88.2 | 81.6 | 77.6 | 57.9 |
| Ex. 1 | Upper (%) | 100.0 | 92.2 | 83.1 | 74.9 | 66.8 | 48.6 |
|  | Lower (%) | 100.0 | 93.9 | 84.2 | 75.8 | 68.5 | 51.7 |
| Ex. 2 | Upper (%) | 100.0 | 92.8 | 83.7 | 75.2 | 67.4 | 49.8 |
|  | Lower (%) | 100.0 | 93.2 | 83.8 | 75.7 | 67.9 | 51.0 |
| Ex. 3 | Upper (%) | 100.0 | 93.7 | 84.5 | 77.0 | 68.5 | 51.2 |
|  | Lower (%) | 100.0 | 94.1 | 86.5 | 77.8 | 70.1 | 53.4 |
| Ex. 4 | Upper (%) | 100.0 | 93.4 | 84.2 | 76.3 | 68.4 | 51.3 |
|  | Lower (%) | 100.0 | 93.3 | 85.3 | 77.3 | 69.3 | 52.0 |

In addition, as shown in the above Table 3, it could be known that when measuring the stabilities of the upper and lower liquid layers after centrifuging the compositions of Comparative Example 1 and Comparative Example 2 produced by not using the spray method, the difference between the upper and lower liquid layers was above 10% difference; but when measuring the stabilities of the upper and lower liquid layers after centrifuging the compositions of Example 1 to Example 4 produced by spraying the cross-linking agent through using the spray method, the difference between the upper and lower liquid layers was within 10% and its stabilities were excellent in a human body. The stability was measured by confirming the maintenance of gel state for 1 week after shaking at 60 rpm velocity after filling a saline solution having 37° C. at 37° C. that is a condition of human body.

While the present invention has been described with respect to the specific embodiments, it will be apparent to those skilled in the art that various changes and modifications may be made without departing from the spirit and scope of the invention as defined in the following claims.

The invention claimed is:

1. A composition preventing tissue adhesion comprising:
a first aqueous solution of:
 a) 1 to 50 wt % of a block copolymer having 1,000 to 500,000 g/mol of molecular weight and comprising a polyethyleneoxide block; and
 b) 0.1 to 4 wt % of a polymer of 10,000 to 1,000,000 g/mol of molecular weight capable of being mixed with the a) block copolymer; and
a second aqueous solution of:
 c) 0.01 to 2 wt % of a cross-linking agent; wherein said composition comprises a combination of the first aqueous solution and second aqueous solution,
 wherein the cross-linking agent is one or more selected from the group consisting of acetate or halide compounds including one or more cations selected from the group consisting of $Mg^{2+}$, $Mn^{2+}$, $Ca^{2+}$, $Cu^{2+}$, $Sr^{2+}$, $Ba^{2+}$, $Fe^{2+}$, and $Co^{2+}$; chitosan; glutaraldehyde; formalin; poly-L-lysine; dopamine; isoleucine, phenylalanine, leucine, threonine, lysine, tryptophan, methionine, valine, histidine, alanine, arginine, asparagine, aspartate, cysteine, glutamine, glutamate, glycine, proline, serine and tyrosine; and
 wherein the second aqueous solution is added into the first aqueous solution at a spraying rate of 10 to 100 ml/min, in which a difference of viscosity between the upper and lower liquid layers is within 10% when centrifuging the composition for 3 minutes at 3,000 rpm and 25° C.

2. The composition preventing tissue adhesion of claim 1, wherein a difference of absorbance between the upper and lower liquid layers is within 10% at 400 to 750 wavelength of visible rays region.

3. The composition preventing tissue adhesion of claim 1, wherein a difference of stabilities between the upper and lower liquid layers is within 10%.

4. The composition preventing tissue adhesion of claim 1, wherein the composition further comprises one or more drugs selected from the group consisting of thrombin, aprotinin, steroidal anti-inflammatory drug and nonsteroidal anti-inflammatory drug (NSAIDs), heparin, and tissue plasminogen activator.

5. The composition preventing tissue adhesion of claim 4, wherein the content of the drug is 0.01 to 50 wt % based on the composition.

6. The composition preventing tissue adhesion of claim 1, wherein the a) copolymer is one or more selected from the group consisting of polyethylene-polypropylene oxide copolymer polyethyleneoxide-polylactic acid copolymer, polyethyleneoxide-polylacticglycolic acid copolymer, and polyethyleneoxide-polycaprolactone copolymer.

7. The composition preventing tissue adhesion of claim 1, wherein the b) polymer is one or more selected from the group consisting of chondroitin sulfate, dermatan sulfate, keratan sulfate, heparan sulfate, alginic acid, hyaluronic acid, carboxymethyl cellulose, dextran, collagen, gelatin, elastin, and fibrin.

8. A method for preparing a composition preventing tissue adhesion, comprising:
preparing a first aqueous solution comprising;
 a) block copolymer having 1,000 to 500,000 g/mol of molecular weight and comprising a polyethyleneoxide block; and
 b) a polymer of 10,000 to 1,000,000 g/mol of molecular weight capable of being mixed with the a) block copolymer; and
adding by spray addition a second aqueous solution comprising c) a cross-linking agent under the spraying rate of 10 to 100 ml/min in a range of 5 to 500 μm of spraying particle diameter over the first aqueous solution to maximize a total area of a surface of the cross-linking agent, together with stirring the combined aqueous solutions under the stirring velocity of 300 to 1500 rpm,
wherein the cross-linking agent is one or more selected from the group consisting of acetate or halide compounds including one or more cations selected from the group consisting of $Mg^{2+}$, $Mn^{2+}$, $Ca^{2+}$, $Cu^{2+}$, $Sr^{2+}$, $Ba^{2+}$, $Fe^{2+}$, and $Co^{2+}$; chitosan; glutaraldehyde; formalin; poly-L-lysine; dopamine; isoleucine, phenylalanine, leucine, threonine, lysine, tryptophan, methionine, valine, histidine, alanine, arginine, asparagine, aspartate, cysteine, glutamine, glutamate, glycine, proline, serine and tyrosine, in which both difference of viscosity and difference of absorbance under 400 to 750 nm wavelength of visible rays region, between the upper and lower liquid layers are within 10% when centrifuging the composition for 3 minutes at 3,000 rpm and 25° C.

9. The method for preparing the composition preventing tissue adhesion of claim 8, wherein the aqueous solution is produced by dissolving the a) copolymer and the b) polymer in a salt solution.

10. The method for preparing the composition preventing tissue adhesion of claim 9, wherein the salt solution is one or more selected from the group consisting of a saline solution, phosphate buffer solution, organic salts buffer solution and bicarbonate buffer solution.

11. The method for preparing the composition preventing tissue adhesion of claim 8, wherein the composition further comprises one or more drugs selected from the group consisting of thrombin, aprotinin, steroidal anti-inflammatory drug and nonsteroidal anti-inflammatory drug (NSAIDs), heparin, and tissue plasminogen activator.

12. The method for preparing the composition preventing tissue adhesion of claim 11, wherein the content of the drug is 0.01 to 50 wt % based on the composition.

13. The method for preparing the composition preventing tissue adhesion of claim 8, wherein the content of the a) copolymer is 1 to 50 wt % based on the composition.

14. The method for preparing the composition preventing tissue adhesion of claim 8, wherein the content of the b) polymer is 0.1 to 4 wt % based on the composition.

15. The method for preparing the composition preventing tissue adhesion of claim 8, wherein the content of the c) cross-linking agent is 0.01 to 2 wt % based on the composition.

* * * * *